United States Patent [19]
Burkholder et al.

[11] 3,968,171
[45] July 6, 1976

[54] PROCESS FOR THE CONTINUOUS ISOLATION OF DIHYDRIC PHENOLS

[75] Inventors: Ward J. Burkholder, Houston; Glenn E. Miller, Pasadena; Fritz J. Nagel, Houston, all of Tex.

[73] Assignee: The Goodyear Tire & Rubber Company, Akron, Ohio

[22] Filed: Mar. 5, 1970

[21] Appl. No.: 16,658

[52] U.S. Cl. .......................... 260/621 A; 260/621 C
[51] Int. Cl.² ......................................... C07C 39/08
[58] Field of Search ...................... 260/621 C, 621 A

[56] References Cited
UNITED STATES PATENTS

| | | | |
|---|---|---|---|
| 2,597,497 | 5/1952 | Joris | 260/621 A |
| 2,989,566 | 6/1961 | Young | 260/621 C X |

FOREIGN PATENTS OR APPLICATIONS

| | | | |
|---|---|---|---|
| 1,034,896 | 7/1966 | United Kingdom | 260/621 C |

*Primary Examiner*—Raymond V. Rush
*Assistant Examiner*—D. B. Springer
*Attorney, Agent, or Firm*—Browning & Bushman

[57] ABSTRACT

Dihydric phenols produced by rearrangement of p-dialkylbenzene hydroperoxides are recovered from the rearrangement effluent by distilling byproduct ketone in a distillation tower from a mixture of the rearrangement effluent with benzene and dihydric phenol-containing aqueous feed and extracting impurities and aromatic byproducts with benzene. Benzene containing dissolved impurities and aromatic byproducts, and water containing the dihydric phenol are removed from the bottom of the distillation tower and separated in an extractor column, the dihydric phenol is recovered from its aqueous solution by crystallization and the mother liquor from the crystallization step is recycled to the distillation tower.

32 Claims, 3 Drawing Figures

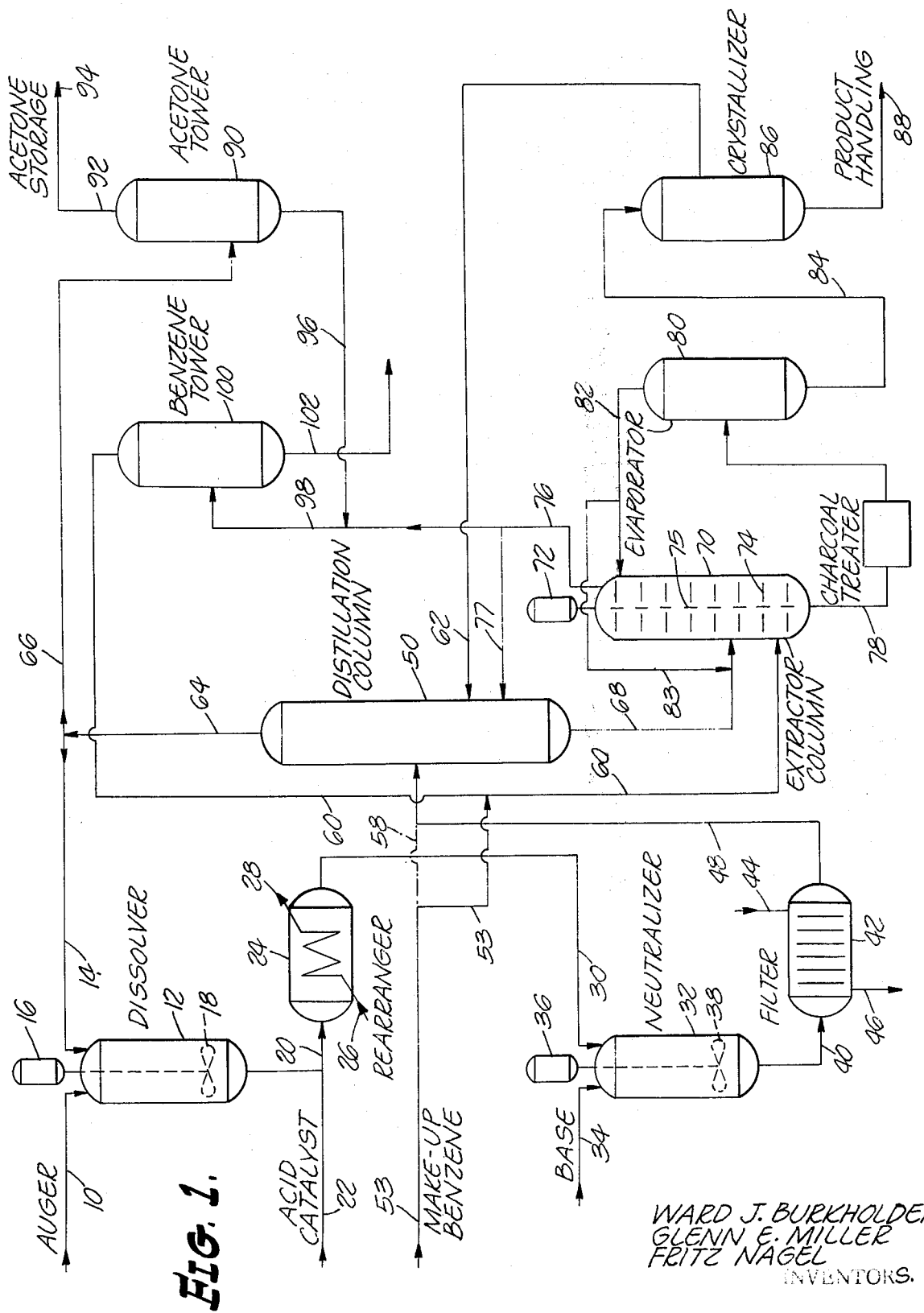

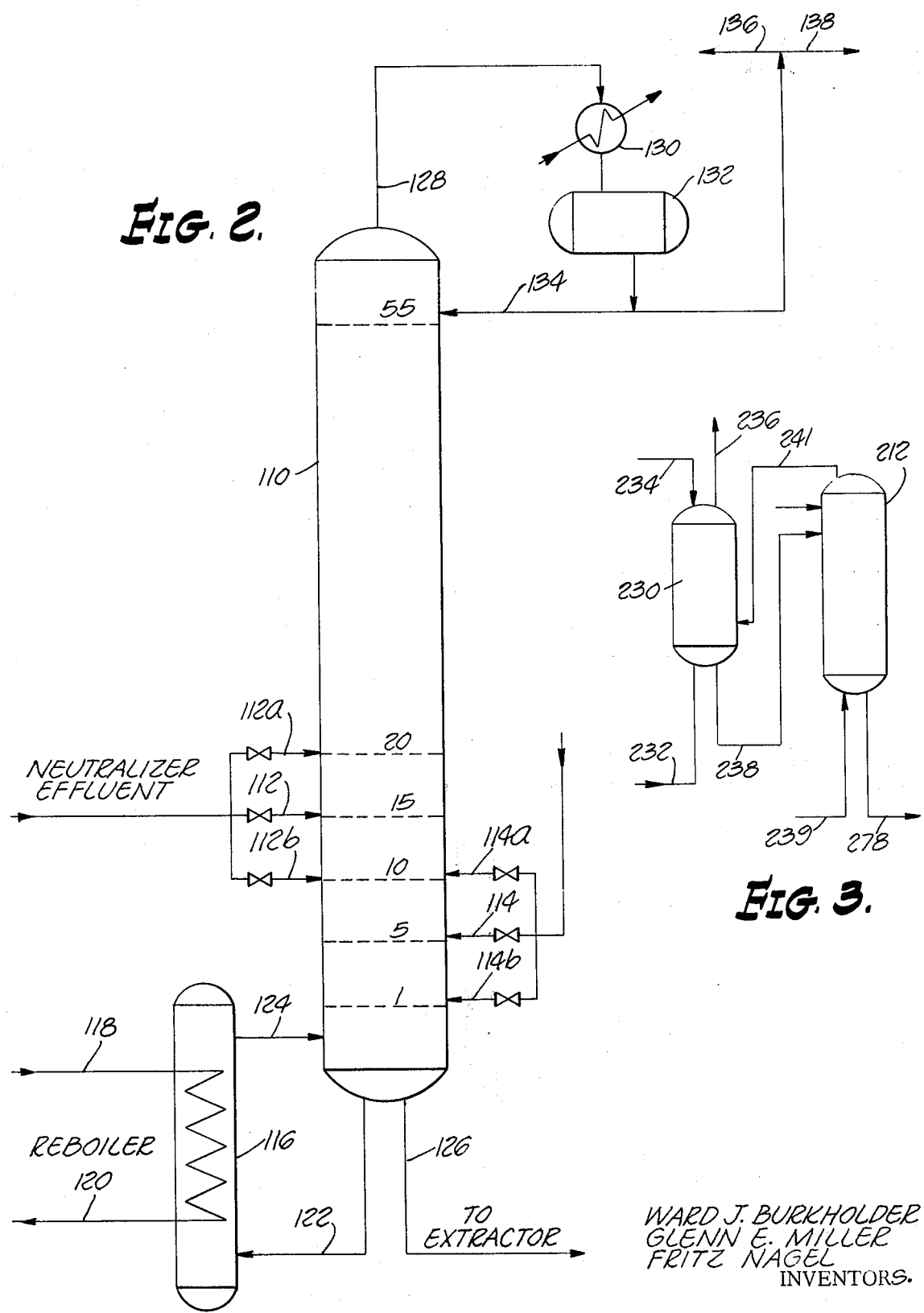

3,968,171

PROCESS FOR THE CONTINUOUS ISOLATION OF DIHYDRIC PHENOLS

FIELD OF THE INVENTION

This invention relates to a process for recovering hydroquinone from rearrangement reaction effluent and, more particularly, to a process for separating byproduct ketone and the aromatic byproducts and impurities from the dihydric phenol product of the rearrangement reaction.

BACKGROUND OF THE INVENTION

Dihydric phenols, hydroquinone and resorcinol for example, are produced according to known processes by the rearrangement of dialkyl benzene dihydroperoxides. Production of resorcinol by rearrangement of m-diisopropylbenzene dihydroperoxide and the production of hydroquinone by the rearrangement of p-diisopropylbenzene dihydroperoxide are well known. In each of these latter processes, a dihydric phenol product and acetone byproduct are produced.

The separation of the hydroquinone or resorcinol from the byproduct acetone and from impurities has been the subject of long and continuing interest. Both hydroquinone and resorcinol, for example, have been recovered by azeotropic distillation from the reaction mixture following addition of a material which forms a low boiling azeotrope with the dihydric phenol of interest. Chlorinated biphenyl, alpha-chloronaphthalene, and other materials which are inert to the dihydric phenol and which form azeotropes of suitable vapor pressure have been used.

DISCUSSION OF THE PRIOR ART

According to one process, the dialkylbenzene hydroperoxide is introduced into a solution consisting of a primary solvent such as benzene, toluene, xylene, and acid catalyst, and a secondary solvent such as the ketone which is produced by the rearrangement reaction. The rearrangement effluent is neutralized and fed to a rectifying column. The secondary solvent is recovered from the rectifying column by distillation and the product hydroquinone is recovered in benzene slurry from the bottom of the rectifying column. The benzene slurry of hydroquinone is filtered and the raw hydroquinone is recrystallized from water. Part of the benzene is recycled to the reactor as the primary solvent. The raw product of this process reportedly contains sufficient dark colored impurity to give the crystals and a solution produced from the product, a brown color.

One of the significant disadvantages of the processes known in the prior art is that certain of these processes require the handling of liquid-solid slurries. Products of this type are difficult to handle, even in specially prepared equipment, because the product tends to form solid layers on all surfaces which may be difficult to remove and because of the tendency of the product to plug filters, valves, conduits, etc. Such problems are particularly serious where it is necessary to handle liquid-solid slurries in distillation apparatus which may include a high surface area wherein frequent cleaning is difficult or impractical. The evaporation of a product solvent in the distillation apparatus may aggravate the problem of solid formation on component surfaces.

These and other disadvantages of the prior art are overcome according to the process of this invention.

SUMMARY OF THE INVENTION

According to the inventive process, dihydric phenols produced by the rearrangement of dialkylbenzene hydroperoxides are separated from byproduct ketones by feeding a neutralized, hydrocarbon-containing, rearrangement effluent stream and an aqueous feed to a distillation tower and recovering separate product and byproduct streams. Distillation heat is supplied to the fluid in the lower section of the tower and the ketone is removed from the upper section of the tower. Bottoms which comprise a product-containing aqueous phase and an impurity-aromatic byproducts containing hydrocarbon phase are removed from the tower. The bottoms hydrocarbon and aqueous phases are fed to an extractor column to extract the aromatic byproducts and impurities into the hydrocarbon phase, and the dihydric phenol extracted from the benzene phase to the water phase, and the phases are separated and the dihydric phenol recovered from the aqueous phase.

According to one feature of the invention, the aqueous feed to the distillation tower is a liquor which contains dissolved dihydric phenol, of the type which is produced by the process. In a more specific feature of this process, a solid product relatively free of byproducts and impurities, is recovered from the aqueous phase by crystallization and the aqueous feed to the distillation tower consists essentially of aqueous mother-liquor from the crystallization.

Certain combinational features of the process are important in producing high quality dihydric phenols with maximum efficiency. For example, the process includes the steps of recycling part of the ketone solvent to the rearrangement reaction step while producing a saleable byproduct ketone of high quality. Another combinational feature of the process comprises the addition of fresh benzene, or equivalent hydrocarbon, to the extractor and then the recycle of benzene, from the extraction step to the distillation tower in a continuous process for permitting separation of product dihydric phenol of high purity.

Other features, advantages, and combinational aspects of the invention will be apparent from the specification which follows and from the drawings to which reference is made.

BRIEF DESCRIPTION OF THE DRAWING

FIG. 1 is a flow diagram illustrating the overall process of this invention.

FIG. 2 is a schematic diagram of the distillation column of this process showing the feed and effluent streams associated therewith.

FIG. 3 is a flow diagram illustrating an alternate process of the present process wherein two extractor columns are employed.

DESCRIPTION OF THE PROCESS

As an aid in understanding the process of this invention, the overall process will be described with reference to the flow diagram illustrated in FIG. 1 with the understanding that this is an exemplary embodiment of the invention and that the process is not limited to the particular arrangement of processing equipment or process streams.

The feed for the process, referred to as wet cake, is introduced through a line 10 to the dissolver 12 along with solvent from a line 14. A homogeneous solution is produced through the agitating action of a motor 16 and an impeller 18.

The wet cake, for producing hydroquinone, for example, is a p-dialkylbenzene dihydroperoxide. For convenience, the process will be described as a method for producing hydroquinone from p-diisopropylbenzene dihydroperoxide. P-di-sec-butylbenzene dihydroperoxide and other para-dialkylbenzene hydroperoxides may, however, be used to produce hydroquinone and analogous metadialkylbenzene hydroperoxides may be selected for producing resorcinol.

In the production of hydroquinone from p-diisopropylbenzene dihydroperoxide, acetone is the preferred solvent for the rearrangement process since acetone is a solvent for the acid catalyst and the dihydroperoxide; acetone is also a byproduct of the rearrangement reaction and additional separation procedures can be avoided by the use of acetone as a solvent, the solvent acetone and the byproduct acetone being removed in the same step. Methylethylketone may, for the same reason, be used as the solvent when a p-disecbutylbenzene dihydroperoxide is used as a source of hydroquinone.

The solvent may consist entirely of acetone but the dissolver usually contains a minor amount of a hydrocarbon, such as benzene. The solvent may be recycled and introduced as part of the solvent stream through the solvent feed line 14, and the recycled solvent usually includes traces of benzene. Similarly the wet cake may include benzene.

The hydroperoxide solution is fed through a line 20, where it is mixed with acid catalyst from catalyst feed line 22, to the rearranger 24. Temperature in the rearranger is maintained by a heat exchange line entering at 26 and exiting at 28, at about 160° F. to 200°F.

Sulfuric acid is illustrative of the type of acid catalyst which may be used in the rearrangement reaction, according to known reactions, $H_3PO_4$, $HClO_4$, p-toluene-sulfonic acid, $SO_2$, $HBF_4$, $H_2SiF_6$, $BF_3$, or any Lewis acid catalyst may be used, generally present in the case of sulfuric acid, in the range of from about 0.1 to 0.8% by weight of the hydroperoxide solution. The rearrangement reaction is generally carried out in the temperature range of from about 50°C to 100°C, with the preferred temperature being about 70°C to 90°C.

The rearranger effluent is fed through a line 30 to the neutralizer 32, a neutralizing base such as ammonia being introduced through a feed line 34, as taught in copending application filed concurrently herewith. Neutralized rearranger effluent is produced through the reason action of a motor 36 and an impeller 38. In addition to ammonia, other basic compounds, such as alkali metal or alkaline earth hydroxides, carbonates, etc., may be used to neutralize the acidic rearrangement effluent. Mild bases such as ammonia and basic salts are preferred.

The neutralized effluent is fed through a line 40 to the filter 42. The filter 42 preferably comprises two or more filter sections through which the neutralized effluent alternately flows. The system is essentially anhydrous, although some water is present by rason of unavoidable admission via dehydration of impurities in the rearrangement reactor. The water content is very low and the water is in solution in the acetone; consequently, the salt formed in the neutralizer comprises solid materials which is separated from the liquid effluent by simple filtration. Before being placed in the process stream again, the filter sections are alternately washed with water to dissolve and remove the solid salts, then the filters dryed by blowing with a gas, such as methane or nitrogen, or by rinsing with anhydrous acetone. The water wash line is indicated at 44 and the salt water removal line is indicated at 46.

The filtered, neutralized rearrangement effluent is fed through liquid effluent feed line 48 to the tower 50. A hydrocarbon benzene for example, is also introduced to the tower 50. In the preferred embodiment of the inventive process, preferably, benzene is introduced to the distillation column 50 as recycle from the extractor column 70 and also from the benzene recovery tower 100. Fresh feed benzene is fed directly to the extractor column 70 through line 53, along with benzene from the benzene recovery tower through line 60. As an alternative arrangement, make up benzene may be fed directly to the acetone distillation column 50, through line 58, (shown in phantom). For convenience, the rearrangement effluent stream which is fed to the distillation column 50 will be regarded as containing benzene which may be introduced at any of the foregoing points.

In addition to benzene, other $C_6$ to $C_{12}$ hydrocarbons may be used as solvents for impurities produced in the various steps of the process, primarily in the rearrangement reaction. Benzene, toluene, ethylbenzene, and xylene, diisopropyl benzene, are preferred, however, any hydrocarbon which will dissolve the impurities but not the dihydric phenol, and which is separable from acetone and will not azeotrope with benzene may be employed. Since the principal function of the hydrocarbon, for example, benzene, is to dissolve and extract the impurities and aromatic byproducts, most any hydrocarbon solvent with this capability is suitable.

When hydroquinone is the desired product, the byproducts are principally p-isopropylphenol and a-hydroxy-p-isopropyl phenol resulting from the cleavage of p-diisopropylbenzene monohydroperoxide and alpha-hydroxy alpha-hydroperoxy-p-diisopropylbenzene (both of which are impurities in the wet cake feed to the rearrangement reactor) and p-isopropenyl phenol resulting from the dehydration of the latter. The impurities formed in the rearrangement reactor include dimers and trimers and other polymers of the product and byproducts, and compounds formed by further reaction of the products and the byproducts. For example, mesityl oxide is formed by the reaction of acetone to diacetone alcohol and its subsequent dehydration. These impurities and byproducts must be removed from the rearrangement product mixture in order to obtain a good color grade product.

In addition to the neutralized, hydrocarbon-containing, rearrangement effluent stream, an aqueous feed is introduced into the tower 50, through line 62, for example. In addition to the product dihydric phenol, then the distillation column feed (rearrangement effluent) includes three major components, acetone, benzene, and water along with impurities and minor constituents not critical to the present process. The acetone is removed by distillation as overhead through line 64. Part of the acetone is recycled through line 14 to the dissolver and part of the acetone is fed through line 68 to the acetone recovery unit. A substantially constant amount of acetone is recycled through the system as described with the acetone which is produced by the rearrangement reaction being removed for purification and sale.

The distillation tower bottoms are removed, through a bottom line 68. The impurity-containing benzene phase is separated from the hydroquinone-containing aqueous phase in the extractor column 70.

The extractor vessel may be of any conventional type for example, contactor type, such as the rotating disc type shown in FIG. 1, or the packed column shown in FIG. 3. It is preferable in order to obtain efficient extraction, to intermix the products countercurrently and for this reason water is fed to the extractor near the top thereof and benzene is fed near the bottom so that the water will pass through the rising benzene layer to extract the dihydric phenol, and the benzene feed will pass through the descending water layer to contact and dissolve any by-products and impurities therein.

The rearrangement reaction mixture from the distillation column 50 is fed through line 68 to extractor column 70 which is shown in this embodiment as a rotary disc contactor having a series of discs 74 mounted on and vertically spaced along shaft 75 which is rotated by a motor 72. Water from evaporator 82, is continuously fed to the extractor vessel 70 through line 82 near the top of the extractor column. Benzene may be fed to the extractor column near the bottom thereof, through lines 53 and 60. The benzene layer formed in the extractor is withdrawn through line 76 near the top of said column with the byproducts and impurities, and benzene is recovered in benzene recovery tower 100, preparatory to reuse of the benzene by recycling to the extractor column. The dihydric phenol is recovered in the water layer formed in said extractor column through line 78, and may be fed to an evaporator 80. Excess water is removed through line 82 and recycled to the extractor column 70, partially to the product feed line 68 through line 83, and partially to the top of the extractor column 70 as the aqueous solvent for the dihydric phenol. The dihydric phenol-rich aqueous liquor from the evaporator 80, is fed through line 84 to the crystallizer 86. Crystalline dihydric phenol, which meets A.S.A. specifications after drying is fed to product handling equipment as indicated at 88.

The mother-liquor from the crystallization is removed and part of the liquor may be given further treatment but, according to the process of this invention, the mother-liquor, which is an aqueous phase containing dissolved product, is recycled through line 62 to the distillation tower, as previously described.

Returning to the handling of the output streams from the distillation tower 50, the acetone separated from rearrangement reaction products is fed through line 66 to the acetone purification tower 90. Substantially pure acetone is removed through an overhead line 92 and sent to acetone storage and handling, as indicated at 94, for sale or on-site use in other processes. The bottoms line 96 returns benzene separated from the product acetone, to join the benzene stream in the line 76 from the extractor column 70; the combined stream, consisting mainly of benzene and impurities with small amounts of water, is fed through line 98 to the benzene recovery tower 100. Purified benzene is recycled through line 60 to the extractor column 70. The phenolic byproducts and impurities separated from benzene in the benzene tower 100, are removed through a bottom line 102, and sent to storage or further recovery processing.

The distillation tower operation is discussed in greater detail with reference to FIG. 2, in which the tower is indicated at 110.

The benzene containing effluent is fed to the tower through one or more input lines indicated at 112, 112a, and 112b, from the neutralizer filter.

An aqueous phase, which is preferably the mother-liquor from the crystallizer, is introduced into the tower through one or more lines shown at 114, 114a, and 114b.

Heat is supplied to the lower section of the tower by circulation of bottoms through a reboiler 116, which is steam heated by means of an input line 118 and a spent steam line 120. The bottoms liquid is fed through a bottoms line 122 to the reboiler and returned to the tower through return line 124. Bottoms product is removed from the tower through another bottom line 126.

Acetone is removed as overhead through a line 128, and a condenser 130 to a reflux drum 132. A large part of the acetone is returned to the tower through a line 134 as reflux, part of the acetone is recycled through a line 136 to the dissolver and part of the acetone is fed through an output line 138 to the acetone recovery and purification system as discussed with respect to FIG. 1.

FIG. 3 is a flow diagram showing an alternative method wherein the extraction of the impurities and byproducts is performed in two extractor columns, column 230 and column 212, which may be similar to the contactor used in the process depicted in FIG. 1 and described above. In the embodiment shown in FIG. 3, the neutralized, solvent stripped rearrangement product mixture is fed to the column 230 through line 232 and the water phase is added to the top of the column through line 234. The hydrocarbon phase is recovered overhead through line 236 and the aqueous product phase from the column 230 is fed to the second stage column 212 through line 238. The operation of the column 212 of FIG. 3 is substantially similar to the operation of the column 230 shown in FIG. 1 and described above. Benzene is fed to column 212 through line 239 and removed to the top and fed to column 230 through line 241. Additional water is fed to column 212 and the extracted aqueous product is recovered through line 278.

The neutralized effluent feed stream to the tower 50 consists essentially of acetone, benzene, hydroquinone and a small amount of water. The effluent feed stream, of course, contains impurities resulting primarily from the rearrangement reaction. These impurities apparently include unidentified dimer, trimer, and polymer reaction products of acetone, hydroquinone, and phenols, as well as certain identifiable impurities such as mesityl oxide, isopropenyl phenol, diisopropylbenzene, isopropyl phenol, etc. Benzene should be present in the distillation column to the extent required to solubilize the impurities present, typically benzene equivalent to about 25 percent of the neutralized feed to column 50. As little as 10 percent, however, may be adequate to effect the extraction.

The hydroquinone content of the feed may be quite variable and is, dependent upon the dihydroperoxide concentration in the dissolver and the conversion efficiency of the rearrangement reaction at any given time. Generally, however, the hydroquinone content will comprise from about 1 to about 15 percent, and preferably from about 5 to about 10 percent of the feed. The water content of the rearranger effluent feed stream does not usually exceed about 5 percent and is normally below about 2 percent.

The aqueous feed to the distillation column generally comprises from about 40 to about 50 percent of the total net feed to the distillation column. The aqueous feed should be sufficient to dissolve all of the dihydric phenol present under the column conditions, and may constitute as little as 10 percent and as great as 60 percent of the total net distillation tower feed.

The distillation tower feed streams may be introduced at any desired temperature. Preferably, however, the feed streams are introduced at a temperature intermediate between the bottoms temperature and the overhead temperature. The bottoms temperature will be determined in accordance with the boiling range of particular hydrocarbon used, for example, with benzene bottoms temperature of about 150° F. to about 180° F. is satisfactory at atmospheric pressure on top of column.

The operating temperature of the distillation column overhead section is a function of the particular solvent being separated from the rearrangement effluent, acetone for example. In the embodiment described as exemplary of the invention, acetone is removed as the column overhead at temperatures generally in the range of from 130° F. to 150° F.

Satisfactory results, on a pilot plant scale were obtained using a distillation column which had 55 trays. Five trays were located between the reboiler section and the aqueous feed injection line 114, ten trays were located between the water injection line 114 and the rearrangement effluent injection line 112, and 40 trays were above the rearrangement feed injection line.

In the distillation column illustrated in FIG. 2, the injection points as described are provided as shown at 112 and 114, with auxiliary injection points as shown at 112a and 112b and at 114a and 114b to permit better control of the tower for more stable operation.

This column could be operated satisfactorily at a reflux ratio of from about 7:1 to about 10:1. These data were considered economical for plant design and commercially satisfactory results were obtained using 9:1 to 10:1 reflux ratios, yielding an overhead composition averaging 0.85 percent water and 1.52 percent benzene.

EXAMPLE I

A material balance calculated around the column as shown in FIG. 2 using distilled water at a flow rate of 6 cc/min as the aqueous phase and a prepared feed at a flow rate of 10 cc/min consisting of 67.34 percent acetone, 22.69 percent benzene, 1.39 percent water, and 8.58 percent hydroquinone gave the following column effluent streams:

The overhead stream, at a flow of 7 cc/min consisted of 97.63 percent acetone, 1.52 percent benzene, and 0.85 percent water.

The water phase of the bottom stream, at a flow of 6 cc/min, consisted of 1.1 percent acetone, 0.92 percent benzene, 14.33 percent hydroquinone and the balance water.

The benzene phase of the bottoms stream, at a flow of 3 cc/min, consisted of 0.73 percent acetone, 98.98 percent benzene, and 0.29 percent water.

While a full pilot plant scale test at the process using toluene was not conducted, laboratory tests of the various steps of the process indicated that toluene and diisopropylbenzene are quite suitable for use in the process as described.

In the preceding discussion, only the steps relating to the inventive process have been discussed. It will be understood, however, that certain other steps which are ancillary to the process may be included. For example, a portion of the crystallization filtrate may be treated with a cationic and ionic beds to remove sulfate, sulfite, etc. which may build up to undesirable levels, to reduce the ion concentration of the aqueous phase. The filtrate, the mother liquor of the crystallization step, contains about 5 to 7 percent hydroquinone and is recycled back to the distillation column.

A commercial scale example of the process is described below as Example II with the understanding that this embodiment of the process and the Examples are intended only to exemplify the process and are not a limitation thereon.

EXAMPLE II

Process feed comprising a mixture of about 37 percent p-diisopropylbenzene dihydroperoxide and about 47 percent benzene, with about 1 percent water and 15 percent other components is dissolved in acetone which contains about 2 percent benzene and 1 percent water. Acid catalyst, sulfuric acid, equal to about 2 weight percent, based upon the hydroperoxide feed, is added to the acetone-hydroperoxide solution and the rearrangement-decomposition reaction is carried at from about 160° to about 200° F for from about 3 minutes to about 15 minutes.

The rearrangement reaction effluent is essentially neutralized with ammonia to a pH meter reading of between about 3.5 and 5.5 and filtered to remove solid salt. The liquid neutralized effluent is introduced into the distillation column.

Mother liquor from the crystallization containing about 7 percent hydroquinone is introduced into the distillation tower at a point below the point of introduction of the effluent feed. A bottoms stream comprising about 21 percent benzene phase and 79 percent aqueous phase is removed from the distillation tower. The aqueous phase comprises about 14 percent hydroquinone and about 1 percent acetone. The benzene phase contains traces of acetone and other byproducts and impurities.

Benzene containing small amounts of hydroquinone, acetone, water, and other impurities is removed from the top of the extractor column to the benzene recovery system for purification.

An aqueous phase consisting of about 12 to 13 percent hydroquinone is removed from the bottom of the extractor column and fed to the evaporator. The evaporator effluent, containing about 20 percent hydroquinone, is cooled to produce product hydroquinone by crystallization and mother liquor which, as previously described, is recycled to the distillation column.

Acetone is purified for non-process use to about 99.5 percent purity with a maximum of 0.5 percent water.

The benzene is treated to remove all byproducts and impurities except a trace of acetone before recycle. A portion of the recycle is fed to the extractor column, according to the embodiment of the process just described, the balance of benzene is recycled to the hydroperoxide production unit.

EXAMPLE III

The rearrangement product stream from the solvent fractionation tower (containing benzene, acetone, water and hydroquinone, with byproducts and impurities) was fed continuously into a packed column. Benzene from an extractor (shown in FIG. 3) was fed countercurrently into the packed column and out to the spent benzene tank. The water stream from the packed column was fed into the extractor countercurrent to fresh benzene, the latter feeding into the packed column and the water solution to the carbon beds. A feed batch of hydroquinone containing 0.54 diisopropylbenzene and 1.19 isopropyl phenol and about 10 percent hydroquinone was fed to the packed column and the water stream from the packed column contained no diisopropylbenzene or isopropyl phenol. It was therefore concluded that the benzene extraction removed essentially all of the impurities from the water without substantial loss of hydroquinone in the benzene.

EXAMPLE IV

The method of Example III, was operated continuously for three days and the results given in Tables I, II, and III which show that most of the impurities dissolve in the benzene in the first column and that only about 0.2 percent hydroquinone dissolves in the benzene.

Table I

GC Analysis of Extraction Columns

| Analysis | Column 230 | | | Extractor 212 | | |
|---|---|---|---|---|---|---|
| | Water In | Benzene Out | Water Out | Fresh Benzene In | Water Out | Benzene Out |
| Mesityl Oxide, % | 0.006 | | | | | |
| p-DIPB, % | 0.001 | 0.14 | | | | |
| p-Isopropylphenol, % | 0.015 | 0.99 | 0.001 | | 0.002 | 0.001 |
| p-Isopropenyl-phenol, % | 0.043 | 1.08 | 0.030 | | 0.025 | 0.002 |
| p-Diisopropenyl-benzene, % | 0.004 | 0.09 | 0.002 | | | |
| p-Isopropenyl-cumene, % | — | 0.053 | | | | |
| Quinone, % | — | 0.028* | | | | |
| Hydroquinone, % | 6.63 | 0.21 | 5.31 | | 6.37 | 0.16 |
| Benzene, % | 0.50 | | | 99.69 | 0.12 | |
| $H_2O$, % | — | | | 0.31 | | |
| DMK, % | 0.02 | 0.11 | 0.06 | Nil | 0.07 | 0.02 |
| Color (ASA Scale) | 3.0 | 1.0 | 1.5-2.0 | 0 | 0.5-1.0 | 0-0.5 |

*Quinone content from 0.19 to 0.45%

Table II

| Time | Sample | Extractor Columns | | |
|---|---|---|---|---|
| | | % p-DIPB | % PIPP | % p-Isopropenylphenol |
| 9:a.m. | E2 Water | 0.002 | 0.003 | 0.017 |
| | E1 Bz[a] | 0.11 | 1.03 | 0.88 |
| 1:p.m. | E2 Water | — | 0.014 | 0.013 |

Table II-continued

| Time | Sample | Extractor Columns | | |
|---|---|---|---|---|
| | | % p-DIPB | % PIPP | % p-Isopropenylphenol |
| | E1 Bz | 0.10 | 0.69 | 1.09 |
| 3:p.m. | E2 Water | 0.004 | 0.050 | 0.019 |
| | E1 Bz | 0.07 | 0.55 | 0.82 |
| | Feed Bz Layer[4] | 0.15 | 1.17 | 1.58 |

Note:
[a]Benzene to waste tank.
[4]Benzene layer from reboiler.

Table III

GC Analysis of Extraction Columns

| Analysis | 1st Column 230 | | | 2nd Column 212 | | | 1st C Bed V-19 | 2nd C Bed V-20 |
|---|---|---|---|---|---|---|---|---|
| | Water In | Bz Out | Water Out | Bz In | Bz Out | Water Out | | |
| Benzene | 0.61 | 99.51[1] | 0.38 | 99.86 | 99.82 | 0.16 | | |
| Acetone | 0.50 | 0.24 | 0.40 | Nil | 0.04 | 0.23 | | |
| Water | 98.89 | 0.25 | 99.22[1] | 0.14 | 0.14 | 99.61 | | |
| Quinone | 0.05 | 0.03 | | | Nil | | | |
| p-Isopropyl-phenol | 0.013 | 1.42 | 0.005 | | 0.022 | Nil | 0.005 | 0.005 |
| p-Isopropenyl-phenol | 0.056 | 2.01 | 0.059 | | 0.029 | 0.036 | 0.015 | 0.003 |
| p-Diisopropyl-benzene | | 0.19 | | | | | | |
| p-Isopropenyl-cumene | | 0.09 | | | | | | |
| Diene | | 0.27 | | | | | | |
| Hydroquinone | 6.43 | 0.27 | 6.12 | | 0.17 | 5.72 | 5.56 | 5.87 |
| Color | −1 | −0.5 | −0.5 | 0 | 0 | −0.5 | 0-0.5 | −0.5 |

[1]This GC analysis is not adjusted for the hydroquinone which does not appear on gas chromatograph.

As the preceding illustrative values and embodiments will indicate, the process as described will produce hydroquinone of high purity without the necessity for subsequent recrystallization, as is generally required with the products of prior art processes. Moreover, problems incident to the production of solid hydroquinone in a distillation column have been completely obviated. This permits more economical design of equipment and lower operating costs, along with a higher quality product as previously described.

It will be understood that the embodiment and values given are included to illustrate and not to limit the invention and that adaptations and modifications may be made by those skilled in the art based upon the principals set forth herein without departing from the spirit and scope of the invention as defined in the following claims.

What is claimed is:

1. In a process for producing dihydric phenols by the rearrangement of dialkylbenzenehydroperoxide wherein a ketone is a byproduct of the rearrangement, the improved process for separating the ketone from the dihydric phenol product which comprises the steps of:
   a. feeding a neutralized rearrangement effluent stream containing said ketone and said dihydric phenol, a hydrocarbon selected from the class consisting of benzene, toluene, xylene, ethylbenzene, diisopropylbenzene and mixtures thereof, and an aqueous feed to a distillation column, the aqueous feed comprising from about 10 to about 60 percent of the total feed to said distillation column and being primarily water;
   b. supplying distillation heat to fluid in the lower section of the column;
   c. removing a stream consisting essentially of the ketone from the upper section of the column;
   d. removing bottoms comprising an aqueous phase and hydrocarbon phase from said column;
   e. separating the hydrocarbon phase from the aqueous phase in an extractor column, water and a hydrocarbon selected from the class consisting of benzene, toluene, xylene, ethylbenzene, diisopropylbenzene and mixtures thereof, being fed to said column to effect countercurrent extraction of said bottoms; and
   f. recovering solid dihydric phenol product from the aqueous phase by crystallization.

2. In a process of the type defined in claim 1, the further improvement wherein the aqueous feed to the distillation column consists essentially of dihydric phenol containing aqueous liquor.

3. The process as defined in claim 1 wherein the hydrocarbon is benzene.

4. The process as defined in claim 1 wherein the step of recovering solid product includes the crystallization of said product from aqueous solvent and wherein the aqueous feed to the distillation tower consists essentially of aqueous mother-liquor from the crystallization step.

5. The process as defined in claim 4 wherein a substantial part of the hydrocarbon is added to the neutralized rearrangement effluent.

6. The process as defined in claim 4 wherein the hydrocarbon is benzene.

7. In a process for producing a dihydric phenol from the class consisting of hydroquinone and resorcinol by the rearrangement of para- or meta-diisopropylbenzene hydroperoxide wherein acetone is a byproduct of the rearrangement, the improved process for separating acetone from said dihydric phenol which comprises the steps of:
   a. feeding a neutralized rearrangement effluent stream containing acetone and said dihydric phenol, a hydrocarbon solvent selected from the class consisting of benzene, toluene, xylene, ethylbenzene, diisopropylbenzene and mixtures thereof, and an aqueous feed to a distillation column, the aqueous feed comprising from about 10 to about 60 percent of the total feed to said distillation column and being primarily water;
   b. heating fluid in the lower section of the column to effect distillation of the acetone;
   c. removing a stream consisting essentially of distilled acetone from the upper section of the column;
   d. removing bottoms comprising a product-containing aqueous phase and an impurity-containing hydrocarbon phase from said column, said hydrocarbon constituting a solvent for dark colored and polymeric impurities resulting from preceding steps;
   e. separating the hydrocarbon phase from the aqueous phase in an extractor column, water and a hydrocarbon selected from the class consisting of benzene, toluene, xylene, ethylbenzene, diisopropylbenzene and mixtures thereof, being fed to said column to effect countercurrent extraction of said bottoms; and
   f. recovering solid product from the aqueous phase by crystallization.

8. In a process of the type defined in claim 7, the further improvement wherein the aqueous feed to the distillation tower consists essentially of aqueous liquor containing said dihydric phenol.

9. In the process as defined in claim 7, the improvement wherein the solid product is recovered by crystallization and wherein the aqueous feed to the distillation tower consists essentially of mother-liquor from the crystallization of the product.

10. A process for manufacturing dihydric phenols comprising the combined steps of:
    a. dissolving a dialkylbenzene dihydroperoxide in a ketone solvent;
    b. introducing an acid catalyst into the ketone solvent;
    c. rearranging and decomposing the hydroperoxide by acid catalysis to form a dihydric phenol product and a ketone byproduct, the ketone solvent being selected to be the same ketone as is produced as a byproduct of the hydroperoxide rearrangement and decomposition reaction;
    d. neutralizing the rearrangement effluent with a basic compound;
    e. removing solid salt formed by the neutralization; introducing the liquid rearrangement effluent containing said dihydric phenol and said ketone; and a hydrocarbon selected from the class consisting of benzene, toluene, xylene, ethylbenzene and diisopropylbenzene and mixtures thereof into a distillation column;
    f. introducing an aqueous feed into said column, the aqueous feed comprising from about 10 to about 60 percent of the total feed to said distillation column and being primarily water;
    g. removing the ketone as overhead from said column;
    h. removing bottoms phase comprising impurity-containing hydrocarbon and dihydric phenol-containing water from said column;
    i. separating the hydrocarbon phase from the aqueous phase in an extractor column, water and a hydrocarbon selected from the class consisting of benzene, toluene, xylene, ethylbenzene, diisopropylbenzene and mixtures thereof, being fed to said column to effect countercurrent extraction of said bottoms; and
    j. recovering the dihydric phenol from the aqueous phase by crystallization.

11. The process as defined in claim 10 wherein the aqueous feed is introduced into said column at a point not higher than the point at which the effluent feed stream is introduced to said column.

12. The process as defined in claim 10 wherein the hydrocarbon is introduced into said column in mixture with the effluent feed stream.

13. The process as defined in claim 10 further comprising the steps of recovering the hydrocarbon phase;
   a. removing impurities from the hydrocarbon; and
   b. recycling the hydrocarbon to the distillation column.

14. The process as defined in claim 10 further comprising the steps of recycling a portion of the ketone from the distillation column to the dissolving step and purifying the remainder of the ketone for non-process use.

15. The process as defined in claim 10 wherein the aqueous feed to the distillation tower contains the dihydric phenol which is produced by the process.

16. The process as defined in claim 10 wherein the hydrocarbon is benzene.

17. The process as defined in claim 16 wherein said dialkylbenzene dihydroperoxide is p-diisopropylbenzene dihydroperoxide.

18. The process as defined in claim 10 further comprising the steps of recirculating mother-liquor from the crystallization step to the distillation column, said mother-liquor comprising the aqueous feed to said column.

19. The process as defined in claim 18 wherein aqueous feed is introduced into the distillation column at a point not higher than the point at which the effluent feed stream is introduced to said column.

20. The process as defined in claim 18 wherein the hydrocarbon is introduced into the distillation column in mixture with the effluent feed stream.

21. The process as defined in claim 18 further comprising the steps of recovering the hydrocarbon phase;
   a. removing impurities from the hydrocarbon; and
   b. recycling the hydrocarbons to the distillation column feed.

22. The process as defined in claim 18 further comprising the steps of recycling a portion of the ketone from the distillation column to the dissolving step and purifying the remainder of the ketone for non-process use.

23. The process as defined in claim 18 wherein the hydrocarbon is benzene.

24. The process as defined in claim 18 wherein said dialkylbenzene dihydroperoxide is a diisopropylbenzene dihydroperoxide and the ketone is acetone.

25. The process as defined in claim 24 wherein the feed to the process is p-diisopropylbenzene dihydroperoxide and the hydrocarbon is benzene.

26. A method for the separation of a dihydric phenol from a rearrangement byproducts and impurities mixture obtained from a neutralized reaction product mixture formed by the acid catalyzed rearrangement of an alkyl aromatic dihydroperoxide, said neutralized reaction product containing said phenol and byproduct ketone, the rearrangement solvent and said ketone having been recovered by fractionation from a total fractionation feed containing at least 10 percent of an aqueous feed being primarily water, comprising the steps:
   a. feeding the rearrangement mixture to an extractor vessel;
   b. adding water to said vessel near the top thereof;
   c. adding a hydrocarbon solvent for said byproducts and impurities, to said vessel near the bottom thereof, said hydrocarbon solvent being selected from the class consisting of benzene, toluene, xylene, ethylbenzene, diisopropylbenzene and mixtures thereof;
   d. intimately intermixing said mixture with said water and said hydrocarbon countercurrently in said extractor vessel;
   e. recovering from said extractor vessel, a hydrocarbon phase containing substantially all of said byproducts and said impurities and substantially none of said phenol;
   f. recovering as bottoms from said extractor vessel an aqueous phase containing said phenol substantially free of said byproducts or impurities; and
   g. recovering said hydroquinone from said water phase by crystallization.

27. The method of claim 26 wherein said extraction is performed in two extractor vessels in series.

28. The method of claim 27 wherein said first extractor vessel in a packed column and said second extractor column is a rotary disc contactor.

29. In a hydroquinone recovery process wherein a rearrangement reaction product mixture containing benzene, hydroquinone and a ketone is neutralized and the rearrangement reaction solvent is recovered therefrom in a distillation column, the feed to said column containing from 10 to 60 percent of an aqueous feed comprising primarily water and wherein said benzene is recovered from said solvent and purified, the improvement for extracting hydroquinone from said neutralized, solvent stripped mixture containing said hydroquinone, said byproducts, and said impurities, comprising the steps:
   a. feeding said neutralized solvent stripped reaction product mixture to an extractor column;
   b. feeding a water stream into said extractor column near the top thereof;
   c. feeding said purified benzene recovered from said solvent to said extractor column near the bottom thereof;
   d. countercurrently contacting said product mixture with said benzene stream and said water stream in said extractor column;
   e. recovering overhead from said extractor column said benzene with said impurities and said byproducts dissolved therein;
   f. recovering from the bottom of said extractor column the water phase containing said hydroquinone substantially free of said impurities and said byproducts; and
   g. recovering said hydroquinone from said water phase by crystallization.

30. The method of claim 29 wherein said rearrangement reaction solvent is a byproduct of said rearrangement reaction.

31. The method of claim 29 wherein said solvent is acetone.

32. In a process for producing dihydric phenols by the rearrangement of dialkylbenzene hydroperoxide wherein a ketone is a byproduct of the rearrangement, the improved process for separating the ketone from the dihydric phenol product which comprises the steps of:
   a. feeding a neutralized rearrangement effluent stream containing said dihydric phenols and said ketone, a hydrocarbon selected from the class consisting of benzene, toluene, xylene, ethylbenzene, diisopropylbenzene and mixtures thereof and an aqueous feed to a distillation column, the aqueous feed comprising from about 10 to about 60 percent of the total feed to said distillation column and being primarily water;

b. supplying distillation heat to fluid in the lower section of the said column;

c. removing a stream consisting essentially of the ketone from the upper section of said column;

d. removing bottoms comprising an aqueous phase and an impurity-containing hydrocarbon phase from said column;

e. feeding said bottoms to an extractor column;

f. feeding a water stream into said extractor column near the top thereof;

g. feeding a make-up stream of said hydrocarbon to said extractor column near the bottom thereof;

h. countercurrently contacting said product mixture with said hydrocarbon stream and said water stream in said extractor column;

i. recovering overhead from said extractor column said hydrocarbon phase with said impurities and aromatic byproducts dissolved therein;

j. separating said impurities and byproducts from said hydrocarbon;

k. recycling said separated hydrocarbon to said extractor column hydrocarbon feed stream;

l. recovering from the bottom of said extractor column the water phase containing said dihydric phenol substantially free of said impurities and said byproducts;

m. partially dehydrating said aqueous dihydric phenol solution withdrawn as bottoms from said extractor;

n. recycling the water removed in step (m) to said extractor column;

o. recovering the dihydric phenol from the partially dehydrated aqueous solution by crystallization; and p. recycling the mother liquor from the crystallization step to said distillation column as said aqueous feed thereto.

* * * * *

UNITED STATES PATENT AND TRADEMARK OFFICE

CERTIFICATE OF CORRECTION

Patent No.: 3,968,171

Dated: July 6, 1976

Inventors: Ward J. Burkholder, Glenn E. Miller and Fritz J. Nagel

It is certified that error appears in the above-identified patent and that said Letters Patent are hereby corrected as shown below:

In Column 3, line 51, delete the word "reason" and insert therefor --agitating--.

In Column 3, line 61, delete the word "rason" and insert therefor --reason--.

In Column 12, line 53, delete the letter "c" and insert therefor --g--.

In Column 14, line 22, delete "in" and insert therefor --is--.

Signed and Sealed this

Fourteenth Day of December 1976

[SEAL]

Attest:

RUTH C. MASON
Attesting Officer

C. MARSHALL DANN
Commissioner of Patents and Trademarks